(12) United States Patent
Kang et al.

(10) Patent No.: US 11,927,576 B2
(45) Date of Patent: Mar. 12, 2024

(54) COMPACT ROCK PYROLYTIC ANALYSIS AND EVALUATION INSTRUMENT

(71) Applicant: INSTITUTE OF GEOLOGY AND GEOPHYSICS CHINESE ACADEMY OF SCIENCES (IGGCAS), Beijing (CN)

(72) Inventors: Shujuan Kang, Beijing (CN); Rixiang Zhu, Beijing (CN)

( * ) Notice: Subject to any disclaimer, the term of this patent is extended or adjusted under 35 U.S.C. 154(b) by 821 days.

(21) Appl. No.: 17/069,226

(22) Filed: Oct. 13, 2020

(65) Prior Publication Data
US 2021/0396726 A1 Dec. 23, 2021

(30) Foreign Application Priority Data
Jun. 18, 2020 (CN) .......................... 202010557493.4

(51) Int. Cl.
*G01N 31/12* (2006.01)
*G01N 1/04* (2006.01)

(52) U.S. Cl.
CPC ............... *G01N 31/12* (2013.01); *G01N 1/04* (2013.01)

(58) Field of Classification Search
CPC .......... G01N 1/44; G01N 25/02; G01N 31/12; G01N 33/241; G01N 25/00
See application file for complete search history.

(56) References Cited

U.S. PATENT DOCUMENTS

2004/0234414 A1* 11/2004 Bezzola ............... G01N 30/466
422/89
2014/0248708 A1* 9/2014 Coleman ................ G01N 30/88
436/158

* cited by examiner

*Primary Examiner* — Jill A Warden
*Assistant Examiner* — Dwayne K Handy

(57) ABSTRACT

A compact rock pyrolytic analysis and evaluation instrument comprises a sample introduction system, a pyrolytic furnace, a bypass system, a total hydrocarbon amount and methane content analysis system, a signal acquisition control system and a computer. The pyrolytic furnace is respectively connected with the sample introduction system and the bypass system, the total hydrocarbon amount and methane content analysis system is connected with the bypass system, the signal acquisition control system is used for controlling and connecting the total hydrocarbon amount and methane content analysis system, and meanwhile, the signal acquisition control system is communicated with the computer. The disclosure simultaneously detects the total amount of hydrocarbons produced by rock pyrolysis and the content of methane gas produced by rock pyrolysis, and the obtained data are reliable.

6 Claims, 16 Drawing Sheets

COMPACT ROCK PYROLYTIC ANALYSIS AND EVALUATION INSTRUMENT

CROSS-REFERENCE TO RELATED APPLICATIONS

The application claims priority to Chinese patent application No. 202010557493.4, filed on Jun. 18, 2020, the entire contents of which are incorporated herein by reference.

TECHNICAL FIELD

The disclosure relates to the technical field of oil and gas resource exploration geological logging, in particular to a compact rock pyrolytic analysis and evaluation instrument.

BACKGROUND

Pyrolytic analysis of rock is mainly to measure hydrocarbon content in rock samples. A sample is heated at a high temperature to generate volatilized or cracked hydrocarbon substances, and the content of the hydrocarbon substances is analyzed such that the type of the organic matter is determined, the abundance of the organic matter in a source rock is evaluated, the oil generation quantity is estimated, the evolution degree of the source rock is determined, and the oil and gas display in a stratum is identified. Among them, the total amount of the gaseous hydrocarbon is shown as S0, and the methane content cannot be accurately detected alone.

At present, the gas detection method for methane mainly adopts a non-dispersive infrared mode and a catalytic combustion mode, but the two methods cannot quantitatively correct the cross interference of background gas such as moisture, and meanwhile, the dust in the process gas needs to be prevented from polluting an optical window in an analysis instrument. Therefore, the sample gas must be removed from dust and moisture through a complex pretreatment system and then sent to gas analysis equipment for detection. And the gas analysis system often has a plurality of defects. For example, the gas sampling and pretreatment system can not meet the requirements of analytical instruments, so that the instruments are easy to damage, and the maintenance and overhaul periods are short; the maintenance workload of the sampling and pretreatment system is large, and the price is high; the response time of the system is delayed, and the requirement of industrial process real-time control cannot be completely met.

SUMMARY

It is an object of the present disclosure to provide a compact rock pyrolytic analysis and evaluation instrument to solve the problems set forth in the above background art.

In order to achieve the above object, the disclosure adopts the following technical solution:

a compact rock pyrolytic analysis and evaluation instrument, wherein the compact rock pyrolytic analysis and evaluation instrument comprises a sample introduction system, a pyrolytic furnace, a bypass system, a total hydrocarbon amount and methane content analysis system, a signal acquisition control system and a computer, wherein the pyrolytic furnace is respectively connected with the sample introduction system and the bypass system, the total hydrocarbon amount and methane content analysis system is connected with the bypass system; the signal acquisition control system is used for controlling and connecting the total hydrocarbon amount and methane content analysis system, and meanwhile, the signal acquisition control system is communicated with the computer.

Further, the compact rock pyrolytic analysis and evaluation instrument, wherein the total hydrocarbon amount and methane content analysis system comprises a total hydrocarbon amount analysis system and a methane content analysis system, wherein the total hydrocarbon amount analysis system comprises a base, a nozzle, a polarization pole probe arm and a collector pole probe arm wherein the nozzle is mounted to the base through a fastening nut, the polarization pole probe arm and the collector pole probe arm are mounted on a detection tower body, the detection tower body is mounted on the pyrolytic furnace through a tower top plate assembly the polarization pole probe arm and the collector pole probe arm are in control connection with the signal acquisition control system, and the methane content analysis system is based on a TDLAS (Tunable Diode Laser Absorption Spectroscopy) methane gas concentration detector.

Further, the compact rock pyrolytic analysis and evaluation instrument, wherein a graphite washer is arranged between the nozzle and the base, the nozzle is made of a ceramic material, and a screw with a screw hole is arranged in the axial direction of the nozzle.

Further, the compact rock pyrolytic analysis and evaluation instrument, wherein two long grooves are formed in the outer wall of the detection tower body, a boss is formed in the inner middle, two round holes are formed between the two long grooves, two internal threads are formed in the radial direction of the detection tower body.

Further, the compact rock pyrolytic analysis and evaluation instrument, wherein the collector pole of the collector pole probe arm is made of stainless steel and is cylindrical in shape, and the upper part thereof is provided with a round groove structure.

Further, the compact rock pyrolytic analysis and evaluation instrument, wherein the bypass system is of a stainless steel structure, wherein the stainless steel structure comprises a disc structure arranged at the upper part, the top part of the stainless steel structure is an internal thread structure connected with the nozzle, the lower part of the stainless steel structure is an external thread structure connected with an outlet of the pyrolytic furnace.

Further, the compact rock pyrolytic analysis and evaluation instrument, wherein the internal passage of the stainless steel structure is of a conical structure, the nozzle and the internal thread structure are directly provided with a sealing gasket, and the disc structure is provided with four round holes and two internal thread holes which are fixedly connected with the detection tower body.

Further, the compact rock pyrolytic analysis and evaluation instrument, wherein the pyrolytic furnace comprises a furnace tube and a pyrolytic furnace pedestal, wherein the furnace tube is installed on the pyrolytic furnace pedestal, the upper part of the furnace tube is welded with the base and connected with a thread structure, and the pyrolytic furnace pedestal is fixed with the bottom plate.

Further, the compact rock pyrolytic analysis and evaluation instrument, wherein the sample introduction system comprises a sample introduction rod assembly, a cylinder assembly and a crucible, wherein the bottom plate is installed on a rack, the sample introduction rod assembly comprises a sample introduction rod and a sliding block, a crucible is installed at the upper end of the sample introduction rod, a sealing gasket is sleeved in the middle of the sample introduction rod, a sliding block is in threaded connection with the lower end the sample introduction rod and the lower end is provided with a fixing nut, a gas path joint is in threaded connection with a side surface of the sample introduction rod and communicated with the sample introduction rod, the sliding block is installed with the bottom plate in a sliding mode, the cylinder assembly comprises a cylinder pedestal and a cylinder installed on the cylinder pedestal, the upper end and lower end of the cylinder are mounted with a sample introduction rod lower speed regulating valve and a sample introduction rod upper speed regulating valve respectively, the top of the cylinder is in threaded connection with the fixing nut, the cylinder pedestal is fixedly connected with the bottom plate, and the gas path joint is connected with the furnace tube.

Compared with the prior art, the disclosure has the following beneficial effects.

Detecting the content of methane gas generated by pyrolysis while detecting the total amount of hydrocarbon substances generated by rock pyrolysis. the disclosure not only detects the content of methane gas generated by pyrolysis, but also detects the total amount of hydrocarbon substances generated by rock pyrolysis, and the obtained data is reliable. The disclosed compact rock pyrolytic analysis and evaluation instrument has a good use effect.

The disclosure discloses an instrument, which is used for sampling at one time and simultaneously completing two kinds of detection and is used for oil and gas exploration and analysis in compact rock.

DETAILED DESCRIPTION OF THE EMBODIMENTS

Figure 1:
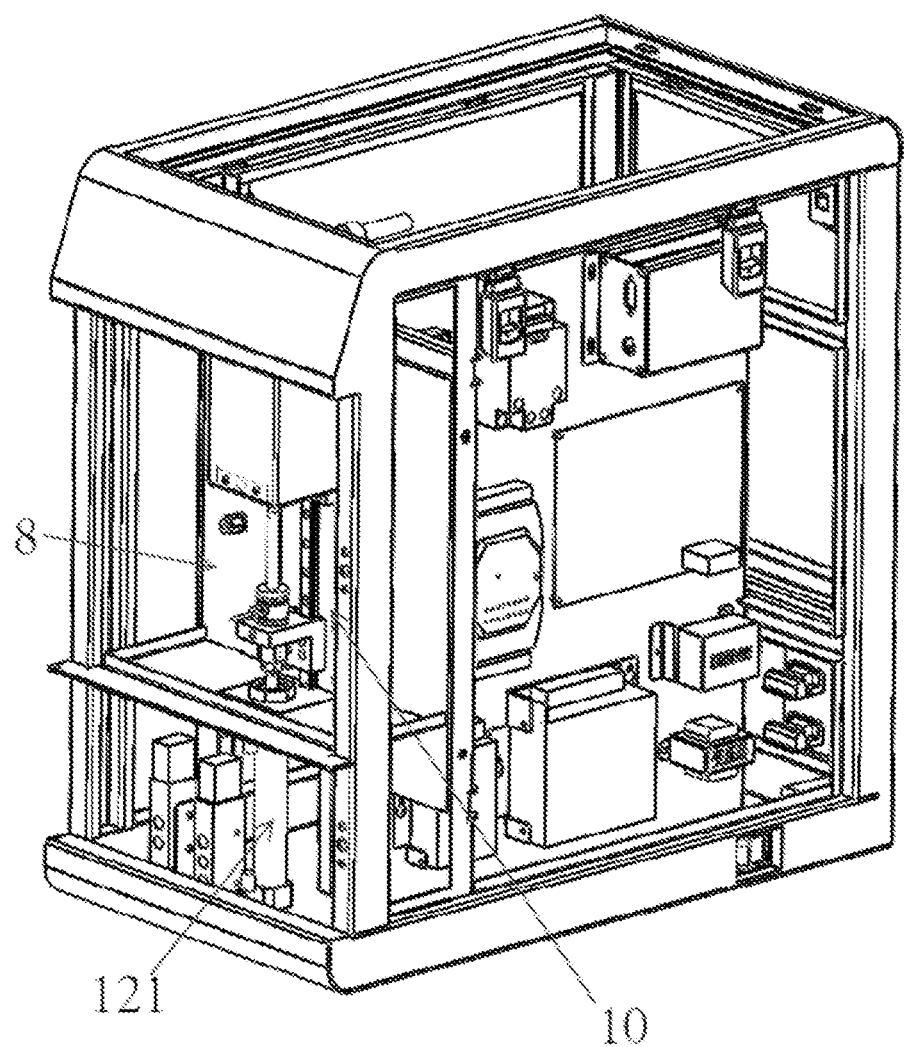
FIG. 1 is a schematic view of an instrument of the present disclosure.
Figure 2:
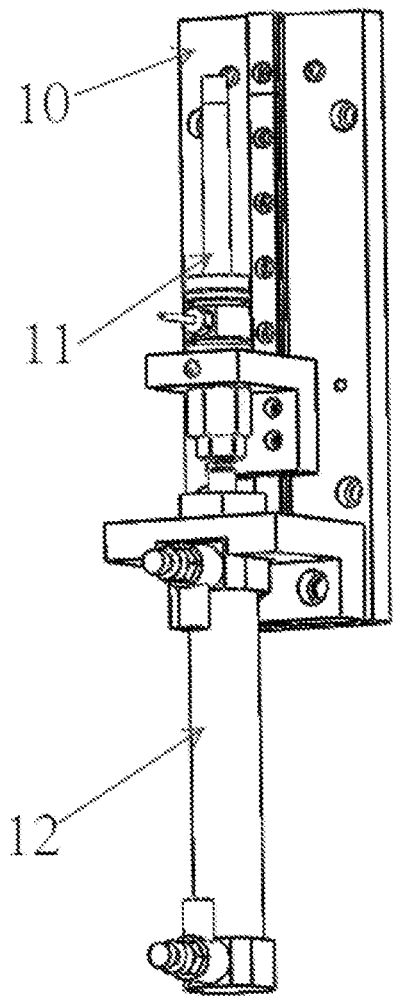
FIG. 2 is a schematic view of a sample introduction system of the present disclosure.
Figure 3:
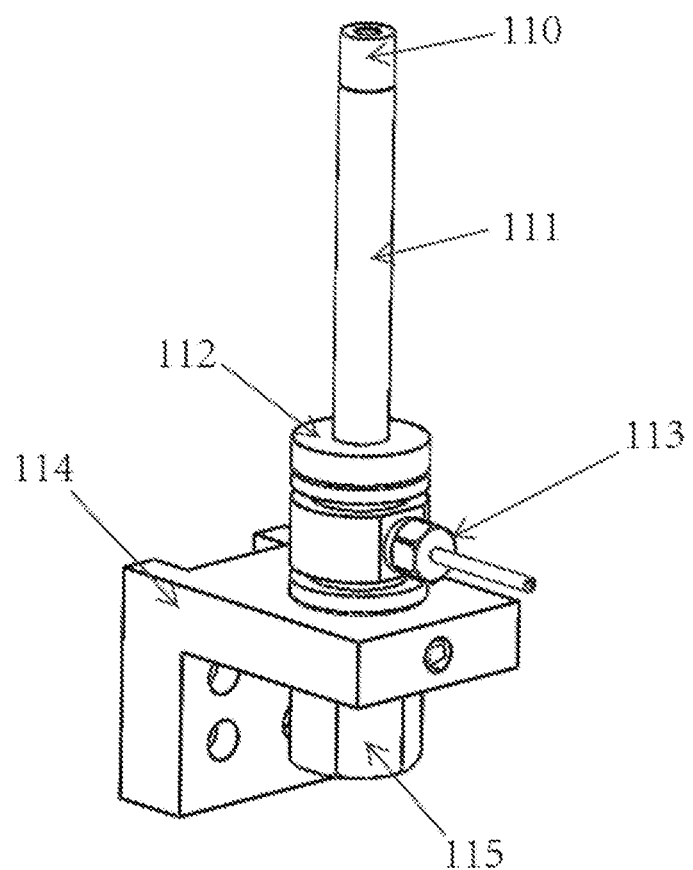
FIG. 3 is an explosive schematic view of a sample introduction rod assembly of the present disclosure.
Figure 4:
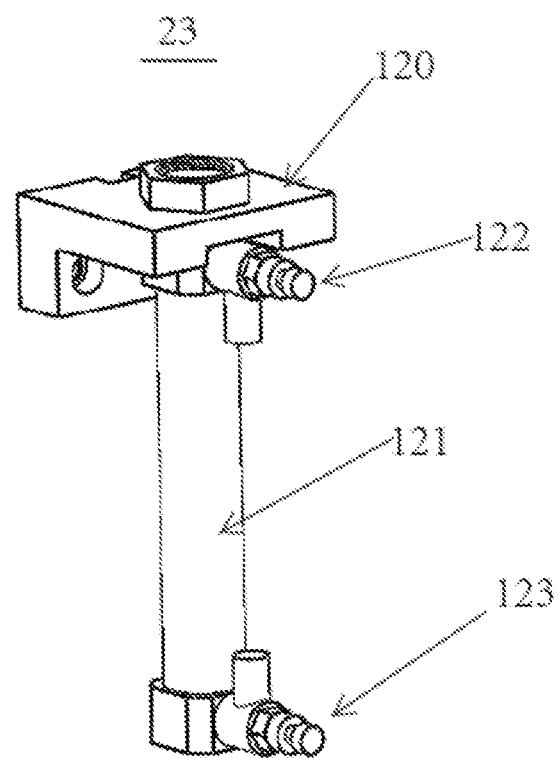
FIG. 4 is a schematic view of a cylinder assembly of the present disclosure.
Figure 5:
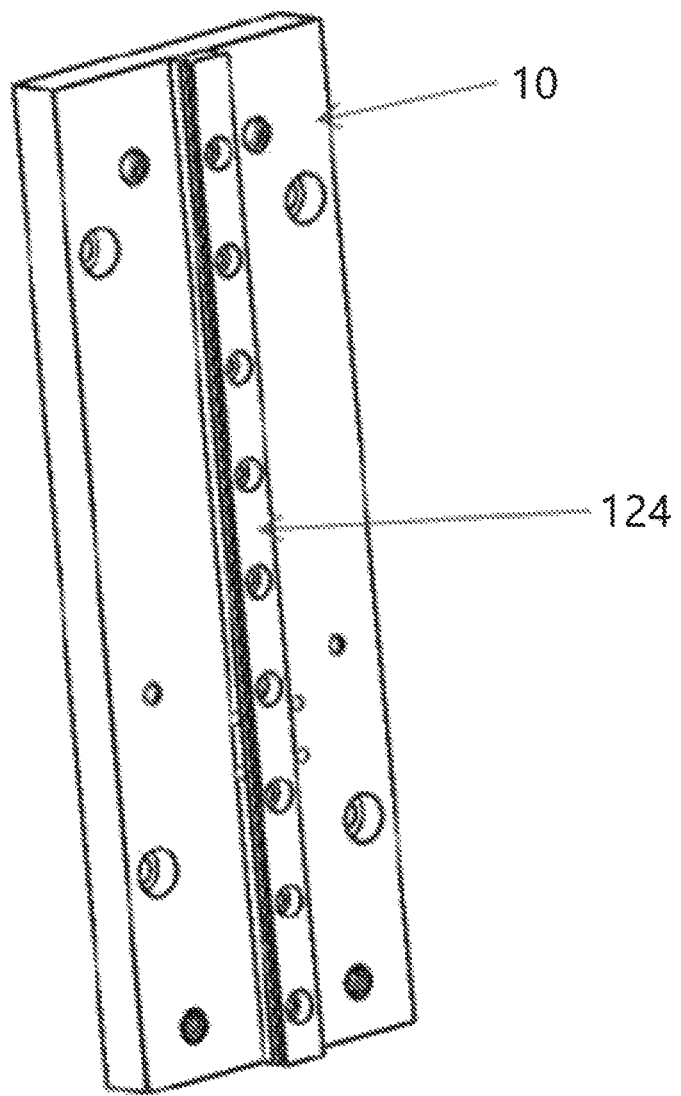
FIG. 5 is a schematic view of a bottom plate of the present disclosure.

The technical solutions in the embodiments of the present disclosure will be clearly and completely described below in conjunction with the accompanying drawings in the embodiments of the present disclosure. Obviously, the described embodiments are only a part of the embodiments of the present disclosure, rather than all the embodiments. Based on the embodiments of the present disclosure, all other embodiments obtained by a person of ordinary skills in the art without involving any inventive efforts are within the scope of the present disclosure.

In the description of the present disclosure, it should be noted that the terms "upper/lower end", "inner", "outer", "front end", "rear end", "both ends", "one end", "other end" and other indications of the orientation or positional relationship is based on the orientation or positional relationship shown in the drawings, and is only for the convenience of describing the present disclosure and simplifying the description, and does not indicate or imply that the device or element referred to must have a specific orientation and be constructed and operated in a specific orientation, therefore cannot be understood as a limitation of the present disclosure. Furthermore, the terms "first" and "second" are used for descriptive purposes only and are not to be construed as indicating or implying relative importance.

In the description of the present disclosure, it should be noted that, unless otherwise clearly specified and defined, the terms "installation", "dispose/sleeve", "socket", "connect", etc. should be interpreted broadly, for example, "connect" can be a fixed connection, a detachable connection, or an integral connection; a mechanical connection or an electrical connection; a direct connection or an indirect connection through an intermediate medium, and a two components' internal connectivity. It will be understood by those of ordinary skills in the art that the specific meanings of the above terms in the present disclosure may be specifically understood.

Referring to FIGS. 1-16, the present disclosure provides a technical solution.

The disclosure discloses a compact rock pyrolytic analysis and evaluation instrument which comprises a sample introduction system, a pyrolytic furnace, a bypass system, a hydrocarbon total amount analysis system, a methane content analysis system, a signal acquisition control system and a computer, the sample introduction system, the pyrolytic furnace and the bypass system are sequentially connected; the total hydrocarbon content analysis system and the methane content analysis system are both connected with a bypass system; the signal acquisition control system controls and is connected with the total hydrocarbon content analysis system and the methane content analysis system; and communication is established between the signal acquisition control system and the computer.

as shown in FIGS. 2-5, the sample introduction system 1 comprises the following three parts: sample introduction rod 111, cylinder 121, and crucible 110. The cylinder 121 adopts a single-cylinder design for controlling the motion of the sample introduction rod 111. A sample is placed into a crucible 110 placed on the upper part of the sample introduction rod 111, the crucible 110 with a sample to be analyzed is carried by the sample introduction rod 111 to enter a pyrolytic furnace 2, and pyrolytic gas is carried by a carrier gas to enter a following total hydrocarbon amount analysis system 4 and a methane content analysis system 5.

The crucible 110 is divided into a main body and an upper cover, and the bottom of the main body and the top of the upper cover are both fine meshes made of nickel-cobalt alloy, and the carrier gas can pass through the fine meshes to carry sample gas into a detector. The sample introduction rod portion is made of 310S stainless steel because it would be subjected to high temperatures in the pyrolytic furnace.

According to the sample introduction system 1, an air cylinder 121 is used as a power execution mechanism to drive the sample introduction rod 111 and the sample to move, and the sample introduction rod 111 is designed to conduct the placement of a sample crucible 110 provide a carrier gas input interface; the bottom plate 10 of the sample introduction system is designed to mount a fixed system rail and ensure that all mechanisms are in the same plane. The cylinder pedestal 120 is designed to realize the connection and fixation of the cylinder 121 and the bottom plate 10, and the sample introduction rod sliding seat (i.e. the sliding block 114) is designed to realize that the cylinder 121 drives the sample introduction rod 111 to move relative to the guide rail 124 on the bottom plate 10.

Figure 6:
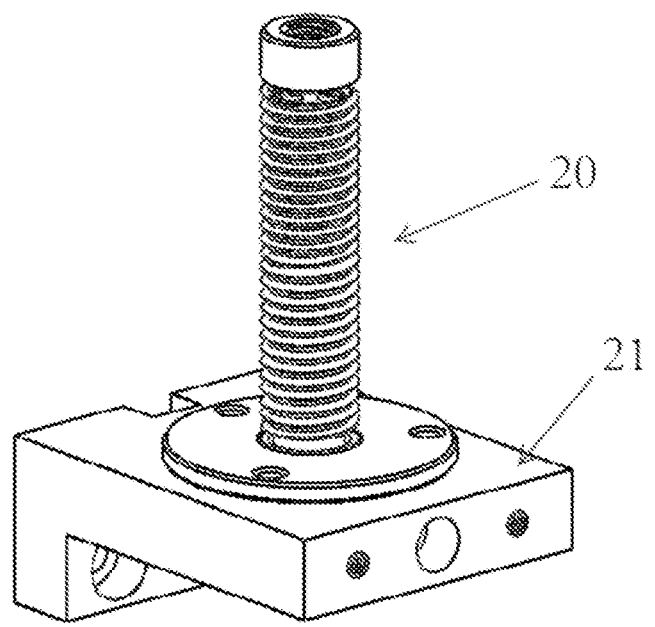
FIG. 6 is a schematic view of a pyrolytic furnace of the present disclosure.

As shown in FIG. 6, the pyrolytic furnace 2 is mainly used for controlling the temperature of the pyrolysis and extracting volatile gas and cracked gas from the sample by high-temperature heating. The structural design of the pyrolytic furnace 2 requires that the dead volume be small and the temperature be controlled accurately, which requires that the heating furnace be small enough and that the conduction efficiency of the pyrolytic furnace be high. The volume of the heating furnace should be small enough so that gases generated by pyrolysis can rapidly enter the detector to be analyzed when carried by the carrier gas, otherwise the dead volume is so large that the generated gases cannot be rapidly measured in real time. Meanwhile, it should be guaranteed that the sample introduction rod can smoothly enter and exit the pyrolytic furnace 2. The pyrolytic furnace 2 is high in conduction efficiency such that the rapid heating is realized, and the furnace wall is as thin as possible. In that way, the heat generated by heating the pyrolytic furnace can be rapidly conducted to the sample, and the rapid cracking of the sample is realized. Meanwhile, in order to realize rapid heating, a heating wire is fully wound on a pyrolytic furnace and fixed by a hose clamp. Since the maximum temperature is to be heated to 600 degrees, 310S stainless steel is used for the pyrolytic furnace material and thermocouples are used for temperature detection. The pyrolytic furnace 2 adopts high-temperature resistant stainless steel 310S; in order to rapidly heat the pyrolytic furnace, a heating wire winding thread (pitch 2, groove depth 1; groove width 1.6; tooth width 0.4) is designed; and the upper part is welded with the FID base. The furnace tube 20 of the pyrolytic furnace 2: inner diameter of 10 mm; an outer diameter of 14 mm; a pyrolytic furnace pedestal 21 to realize the fixation of the pyrolytic furnace 2 and the bottom plate 10 and to ensure that the pyrolytic furnace 2 and the sample introduction rod 111 are on the same plane; material: aluminum.

Since the total amount of hydrocarbons is to be analyzed and the methane content is also to be detected, the system divides the gas generated by the pyrolysis into two paths to analyze the total amount of hydrocarbons and the methane content respectively.

Since the gas produced by the pyrolysis includes methane and heavy hydrocarbon gas, it is necessary to ensure that the gas supplies a rapid analysis of the total amount of the hydrocarbons in the case of a high temperature gaseous state, while a path of gas is separated from the opening of the pyrolytic furnace 2.

Because the space of the pyrolytic furnace is limited at present, and the pyrolytic gas needs to be rapidly split for the methane content detection under the condition that the analysis of the total amount of the hydrocarbons is not influenced, the position and the structure of the opening are the keys to whether the gas path can smoothly flow out the gas.

Figure 7:
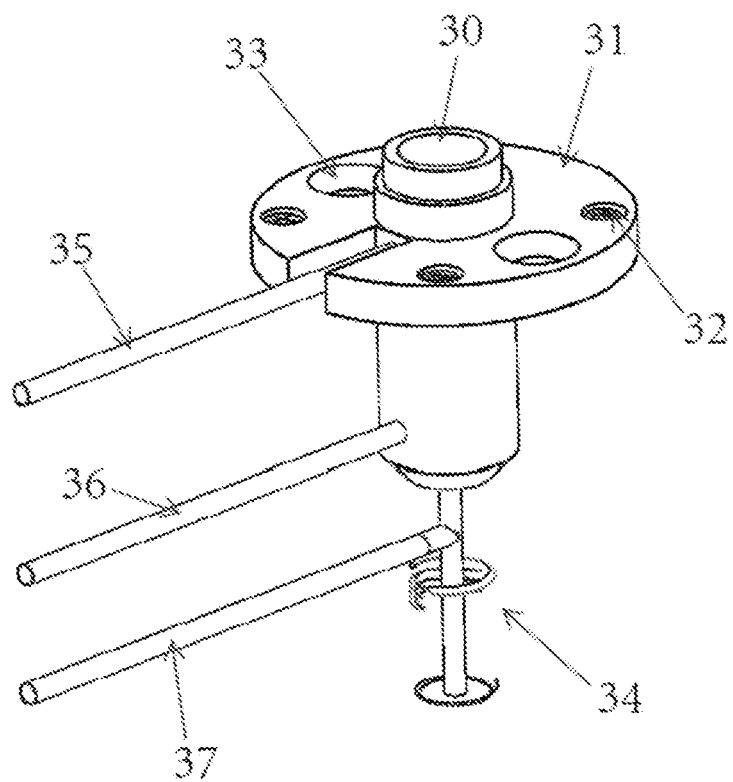
FIG. 7 is a schematic diagram of a bypass system according to the present disclosure.
Figure 8:
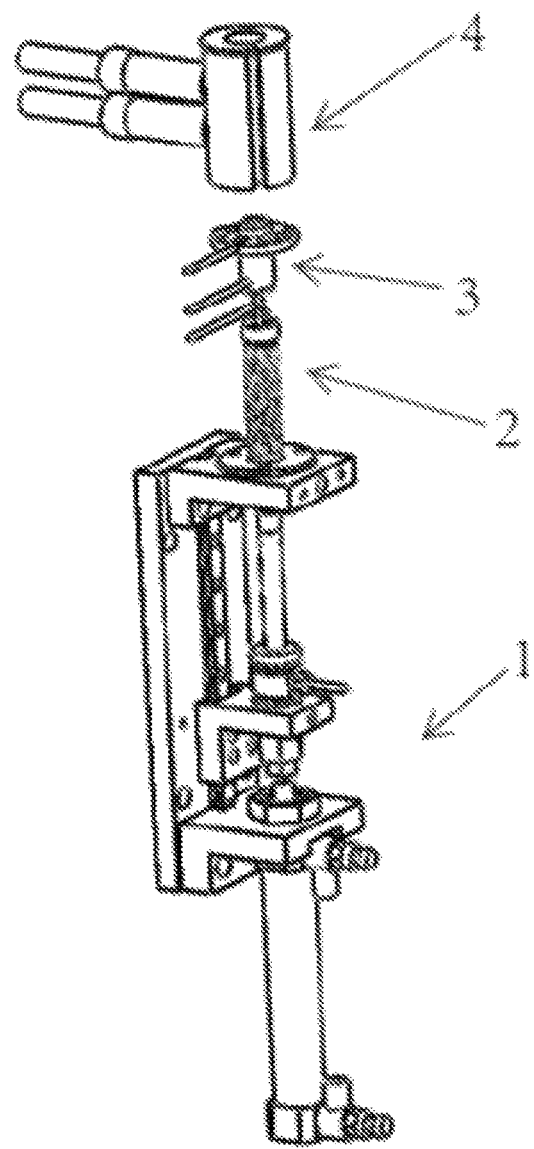
FIG. 8 is an explosive schematic view of a sample introduction system of the present disclosure.
Figure 9:
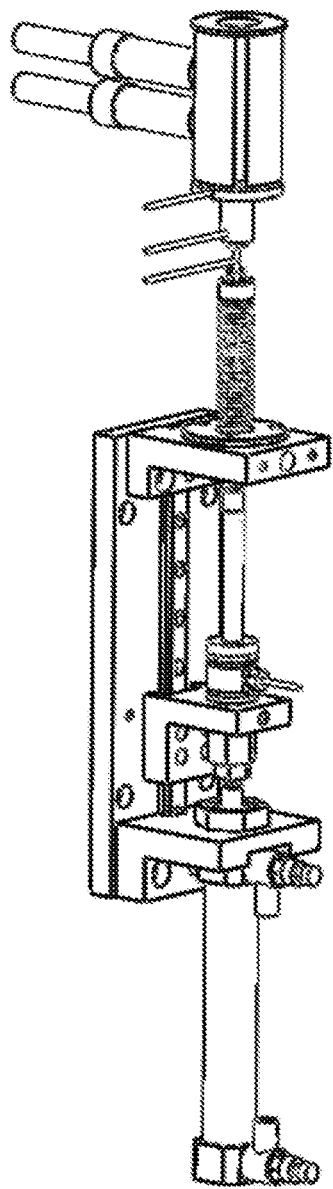
FIG. 9 is a schematic view of the assembly of FIG. 8 of the present disclosure.

As shown in FIGS. 7-9, the bypass system 3 integrally adopts a stainless steel structure, so that the high-temperature resistance, oxidation resistance, rust resistance and corrosion resistance performance of the FID are guaranteed; the connection part of the top and the nozzle 43 is designed as an internal thread structure 30 so that the connection with the nozzle 43 is convenient, and the internal passage is designed as a conical structure so that the sealing performance of the sealing gasket part when the nozzle 43 is connected is ensured; the upper part is designed as a disc-type structure 31, four round holes which are fixedly connected with equipment and two internal thread holes which are fixedly connected with the detection tower body 46 are designed, so that the whole FID is convenient to install and fix and the replacement and maintenance at the later stage are convenient; the lower part is designed as an external thread structure 34 so that later-stage installation and maintenance can be rapidly realized and it is butted with the outlet of the sample gas path (pyrolytic furnace 2) of the instrument; the combustion-supporting gas path, the fuel gas and the sample gas bypass gas path (35-37) are designed as stainless steel pipelines of $\varphi 1.6$, and are welded with the base 40 into a whole, so that the tightness of the connection between the gas path and the base 40 is ensured and the connection between the gas path and the external fuel gas and the combustion-supporting gas path is convenient; in the gas path of the bypassed sample gas for detecting the methane content, the gas resistance is used for balancing so that the pyrolytic gas can not only complete the analysis of the total amount of hydrocarbons, but also meet the requirement of rapid bypass for detecting the methane content.

The pyrolytic furnace temperature control range is 90° C.-600° C. The evaluator also has a temperature control system for controlling the temperature of the heating furnace, which is part of the instrument. The temperature control system adopts the preferred incremental PID control.

For the analysis of the total amount of hydrocarbons or methane content, detectors are essential key parts. The detector is capable of converting the amount of the detected substance into a corresponding electrical signal to be detected by the signal acquisition system. For the pyrolytic analysis part, the total hydrocarbon amount detector mainly detects the content of hydrocarbons, and the methane detector mainly detects the content of the methane gas.

Figure 10:
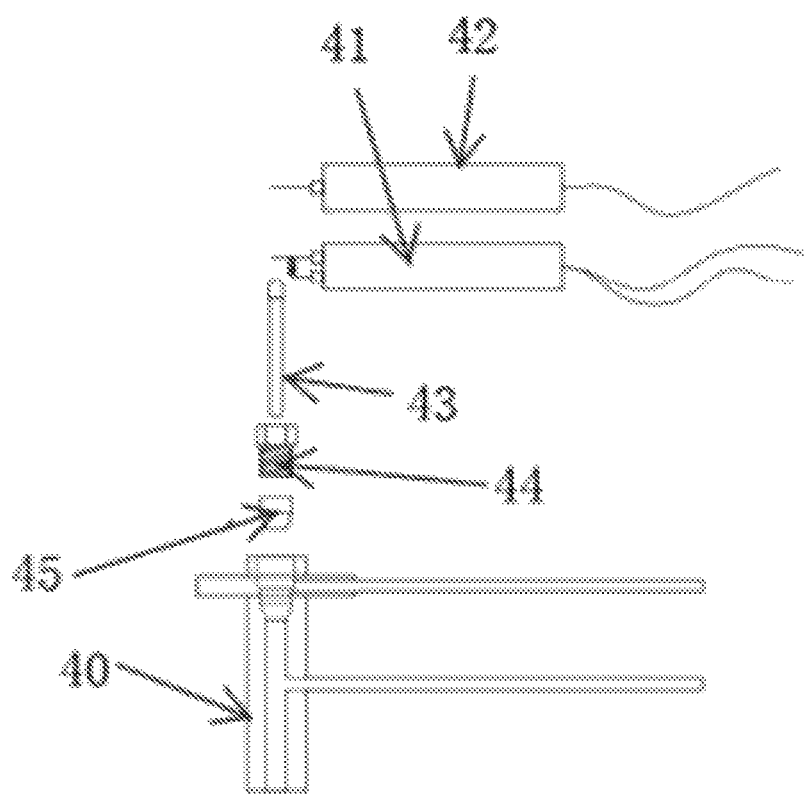
FIG. 10 is a schematic diagram of a total hydrocarbon analysis system of the present disclosure.
Figure 11:
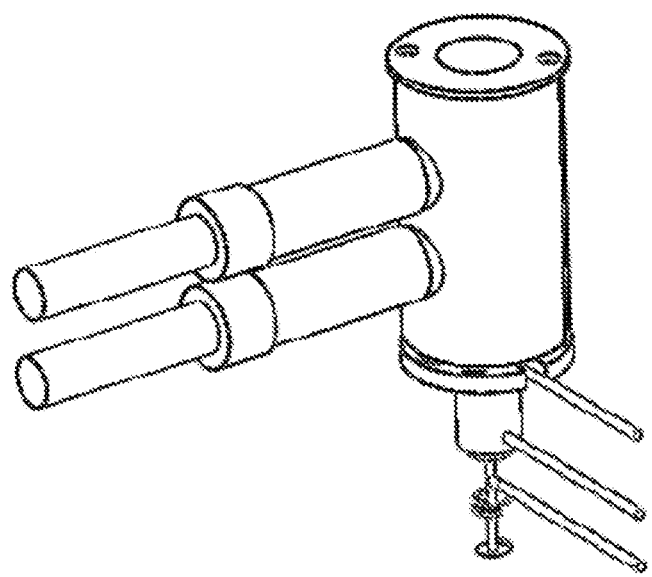
FIG. 11 is a schematic three-dimensional view of FIG. 10 of the present disclosure.
Figure 12:
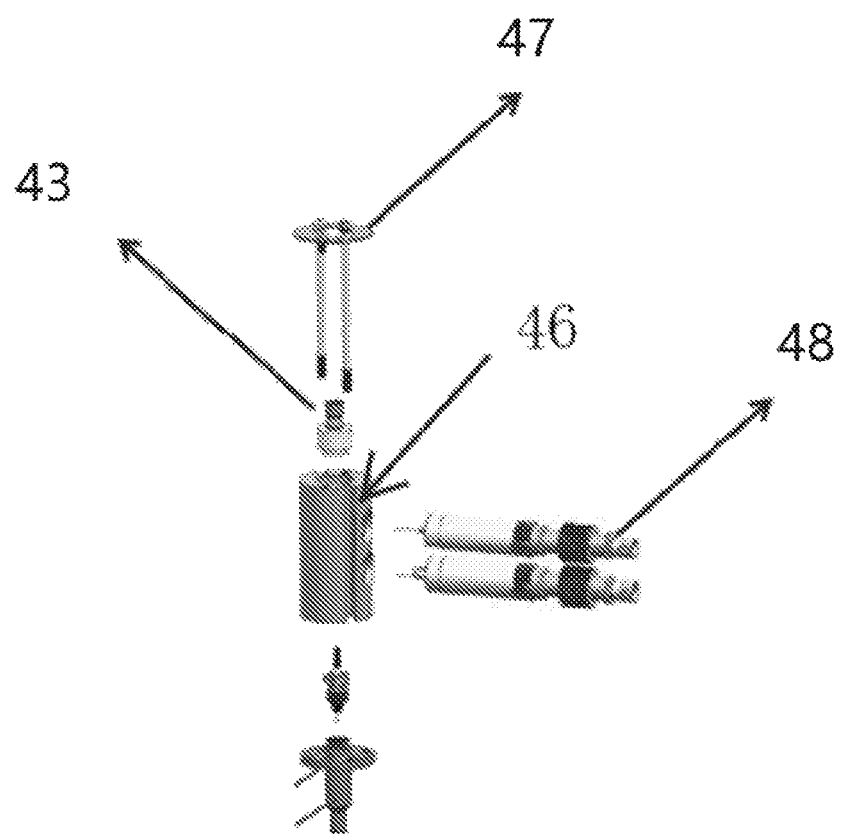
FIG. 12 is an explosive schematic view of FIG. 11 of the present disclosure.

As shown in FIGS. 10-12, the type of detector that the instrument employs is a mass detector capable of detecting the mass concentration of carbon-containing organics in the sample gas. The relative response values for all hydrocarbon compounds (carbon number$\geq 3$) are almost equal, as are the relative response values for a homologue (carbon number$\geq 3$) in heteroatom-containing hydrocarbon organics. For pyrolytic analysis, it can be considered that the response value of the detector to various carbon-containing organics is linear with the mass.

It is mainly composed of base 40, nozzle 43, polarization pole probe arm 41, collector pole probe arm 42, etc. Since the hydrocarbon substance detected by pyrolytic analysis is a hydrocarbon substance volatilized from 90° C. to 600° C., in order to prevent the condensation of the sample gas from clogging the nozzle 43, a heat insulating block is added outside the detector.

The sample gas is combined with hydrogen at the base 40 under the driving of carrier gas (nitrogen) and flows into the nozzle 43 from below the nozzle 43. The air flows out from the side surface of the base 40 as the combustion-supporting air to provide an aerobic environment for the nozzle 43.

The polarization pole probe arm 41 is composed of a polarization pole probe and an ignition coil to accomplish the task of providing a polarization electric field and ignition. Before the detection, alternating current (6 V/AC) is applied to the two ends of a lead wire of the polarization pole probe arm 41 so that the ignition coil is heated to finish ignition; after the ignition, the two ends of the lead wire of the probe arm are switched to be DC-300V to provide a polarization electric field to the detector. The collector pole probe arm 42 is fixed above the polarization pole probe arm 41 and collects the ion current generated by the detection.

Figure 13:
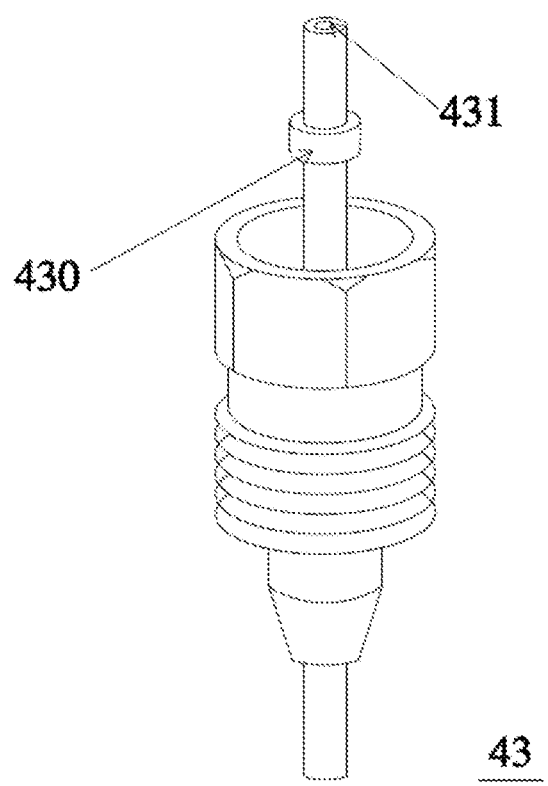
FIG. 13 is a schematic view of a nozzle of the present disclosure.

As shown in FIG. 13, a ceramic material is adopted in the design of the nozzle 43, so that the contact between a sample and hot metal can be avoided; the catalysis and adsorption of components, particularly polar or chemically active components, can be reduced; the peak shape is normal, and the noise is small. A special screw is designed to connect the nozzle 43 with the base 40 and the combustion-supporting gas reaches above the nozzle 43 through a small hole 431 in the nut 44. The sealing gasket is made of graphite materials so that the high-temperature resistance of the FID is improved while the sealing performance is guaranteed.

Figure 14:
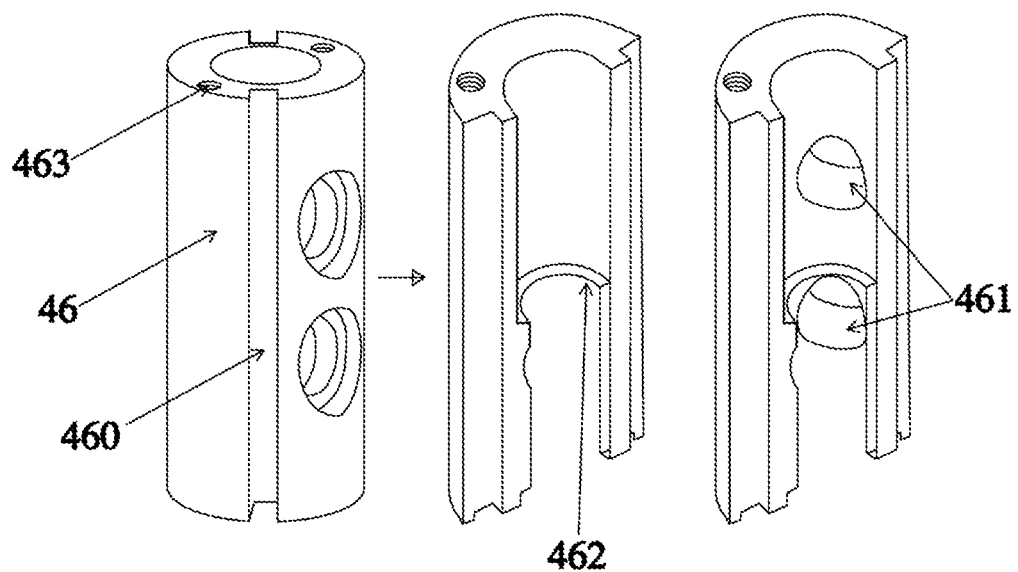
FIG. 14 is a schematic view of a detection tower body of the present disclosure.

As shown in FIG. 14, the detection tower body 46 is made of stainless steel material to ensure the high temperature resistance, oxidation resistance, rust resistance and corrosion resistance of the FID, and two long grooves 460 are externally designed to fixedly mount the detection tower body on the base 40; two round holes 461 are designed in the middle of the outer part to realize the connection and fixation of the signal probe fixing seat, the ignition and the polarization pole probe fixing seat; a platform structure is designed in the middle of the inner part so that the later-stage collector pole is facilitated and the outer ceramic insulator can be conveniently mounted and fixed; the upper part is provided with two internally thread holes 33 for mounting and fixing the metal plate on top of the tower.

Figure 15:
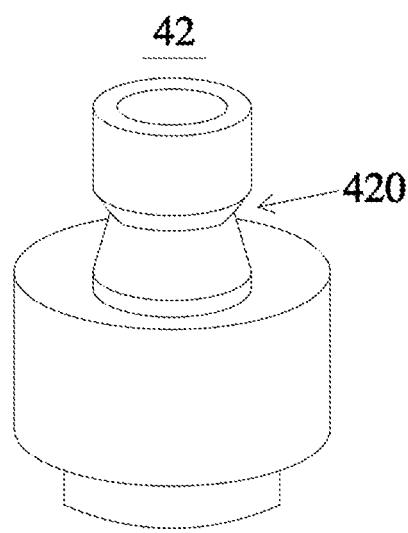
FIG. 15 is a schematic view of a collector pole probe arm of the present disclosure.
Figure 16:
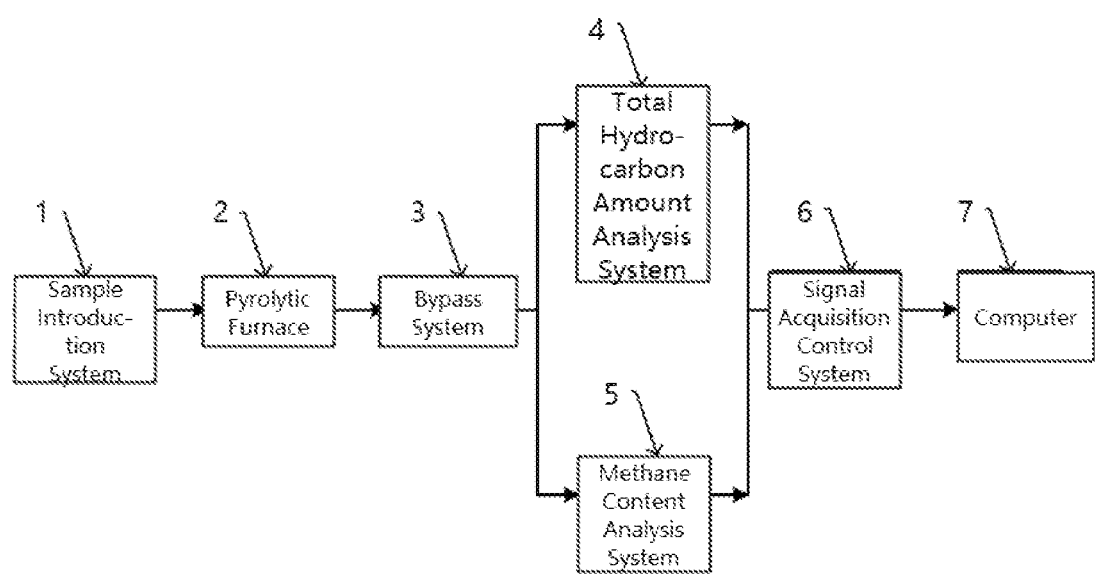
FIG. 16 is a block diagram of the system of the present disclosure.

As shown in FIG. 15, in the collector pole assembly (collector pole probe arm 43), the collector pole is made of stainless steel and is cylindrical in shape, so that the collecting performance of the ion current is ensured; a round groove structure 420 is designed on the upper part and used for realizing tight connection with the collector pole probe. In order to ensure excellent insulation with the nozzle 43, a high-purity ceramic is adopted for the collector pole insulation material such that the insulation resistance can reach 1015-1018Ω and the nozzle can resist 300° C. high temperature; the ceramic insulator adopts a cylindrical mesa structure so that the collector pole assembly can be conveniently connected and fixed with the detection tower body 46.

A signal probe assembly 48 is designed with a special probe fixing seat, one end of is of a cylindrical mesa structure for convenient connection and fixation with the detection tower body, and one end is designed to be of an external thread structure so that the connection and fixation with the signal probe part is facilitated; the connecting part of the signal probe and the collector pole is designed into a fork structure so that the tight connection with the collector pole cylinder and the collection of an ionization signal are guaranteed; ceramic materials are adopted in the insulating part so that the insulating property is guaranteed and the interference of external signals is avoided; in order to ensure the sealing property of the signal probe part, the signal probe part and the probe fixing seat part are sealed by adopting a sealing ring, and the sealing ring adopts a polytetrafluoroethylene material to ensure the high-temperature resistance; in order to improve the anti-interference ability of the collector pole signal and facilitate the connection with amplification circuit, BNC joint is used; The ignition and polarization pole probe assembly is designed with a special probe fixing seat, one end of is of a cylindrical mesa structure for convenient connection and fixation with the detection tower body, and one end is designed to be of an external thread structure so that the connection and fixation with the signal probe part is facilitated; the polarization pole probe is designed into a U-shaped fork type structure so that the sample is convenient to burn and ionize; the ignition wire is made of a nickel-chromium wire material such that the low-voltage automatic ignition is convenient, and the insulation part is made of a ceramic material so that the insulation performance and the interference to external signals are guaranteed in order to ensure the sealing property of the probe part, the signal probe part and the probe fixing seat part are sealed by adopting a sealing ring, and the sealing ring adopts a polytetrafluoroethylene material to ensure the high-temperature resistance; in order to connect with the power supply and the control circuit conveniently, a BNC joint is used; The methane content analysis system 5 is based on a TDLAS (Tunable Diode Laser Absorption Spectroscopy) methane gas concentration detector, so that the influence of environmental temperature and humidity and interference gas is avoided.

While embodiments of the present disclosure have been shown and described, it will be understood by those skilled in the art that various changes, modifications, substitutions and alterations may be made herein without departing from the principles and spirit of the disclosure, the scope of which is defined by the appended claims and their equivalents.

What is claimed is:

1. A compact rock pyrolytic analysis and evaluation instrument, comprising a sample introduction system, a pyrolytic furnace, a bypass system, a total hydrocarbon amount and a methane content analysis system, a signal acquisition control system and a computer, wherein the sample introduction system comprises a sample introduction rod assembly, a cylinder assembly and a crucible, the sample introduction rod assembly comprises a sample introduction rod and a sliding block, the crucible is installed at an upper end of the sample introduction rod and the cylinder assembly comprises a cylinder pedestal and a cylinder installed on the cylinder pedestal, the cylinder assembly is coupled to the sample introduction rod assembly, the sliding block and the cylinder pedestal are connected to a bottom plate, wherein the crucible is configured to place a rock sample to be further carried by the sample introduction rod into the pyrolytic furnace for analysis;

the pyrolytic furnace comprises a furnace tube installed on a pyrolytic furnace pedestal, an upper part of the furnace tube is welded with a base of the total hydrocarbon amount and methane content analysis system and connected with a thread structure, the pyrolytic furnace pedestal is fixed with the bottom plate, wherein the pyrolytic furnace is configured to heat the rock sample at high temperatures for rapid cracking of the sample to extract volatile gas and cracked gas from the sample;

the bypass system is a stainless steel structure comprising a disc structure arranged at an upper part, a top part of the stainless steel structure is an internal thread structure connected with a nozzle, a lower part of the stainless steel structure is an external thread structure connected with an outlet of the pyrolytic furnace and stainless steel pipes comprising a combustion-supporting gas path, a fuel gas path and a sample gas bypass gas path are welded with the base of the total hydrocarbon amount analysis system; and the total hydrocarbon amount and methane content analysis system comprises a total hydrocarbon amount analysis system and a methane content analysis system, the total hydrocarbon amount analysis system comprises the base, the nozzle, a polarization pole probe arm and a collector pole probe arm, wherein the nozzle is mounted to the base through a fastening nut, the polarization pole probe arm and the collector pole probe arm are mounted on a detection tower body, the detection tower body is mounted on the pyrolytic furnace through a tower top plate assembly, the polarization pole probe arm and the collector pole probe arm are in control connection with the signal acquisition control system, and the methane content analysis system comprises a tunable diode laser absorption spectroscopy (TDLAS) methane gas concentration detector;

wherein the pyrolytic furnace is respectively connected with the sample introduction system and the bypass system, the total hydrocarbon amount and methane content analysis system is connected with the bypass system; the signal acquisition control system is used for controlling and connecting the total hydrocarbon amount and methane content analysis system, and the signal acquisition control system is communicated with the computer.

2. The compact rock pyrolytic analysis and evaluation instrument of claim 1, wherein a graphite washer is arranged between the nozzle and the base, the nozzle is made of a ceramic material, and a screw with a screw hole is arranged in an axial direction of the nozzle.

3. The compact rock pyrolytic analysis and evaluation instrument of claim 1, wherein two long grooves are formed in an outer wall of the detection tower body, a platform structure is designed in middle of an inner part of the detection tower body, two round holes are formed between the two long grooves, two internal threads are formed in a radial direction of the detection tower body.

4. The compact rock pyrolytic analysis and evaluation instrument of claim 1, wherein the collector pole of the collector pole probe arm is made of stainless steel and is cylindrical in shape, and an upper part of the collector pole probe arm is provided with a round groove structure.

5. The compact rock pyrolytic analysis and evaluation instrument of claim 1, wherein the internal passage of the stainless steel structure is of a conical structure, the nozzle and an internal thread structure are directly provided with a sealing gasket, and the disc structure is provided with four round holes and two internal thread holes which are fixedly connected with the detection tower body.

6. The compact rock pyrolytic analysis and evaluation instrument of claim 1, wherein the bottom plate is installed on a rack, a sealing gasket is sleeved in a middle of the sample introduction rod, the sliding block is in threaded connection with a lower end of the sample introduction rod and the lower end is provided with a fixing nut, a gas path joint is in threaded connection with a side surface of the sample introduction rod and communicated with the sample introduction rod, the sliding block is installed with the bottom plate in a sliding mode, an upper end and a lower end of the cylinder are mounted with a sample introduction rod lower speed regulating valve and a sample introduction rod upper speed regulating valve respectively, a top of the cylinder is in threaded connection with the fixing nut, the cylinder pedestal is fixedly connected with the bottom plate, and the gas path joint is connected with the furnace tube.

* * * * *